US005525510A

United States Patent [19]

McCabe et al.

[11] Patent Number: 5,525,510

[45] Date of Patent: Jun. 11, 1996

[54] COANDA EFFECT GENE DELIVERY INSTRUMENT

[75] Inventors: Dennis E. McCabe, Middleton; William F. Swain, Madison, both of Wis.

[73] Assignee: Agracetus, Inc., Middleton, Wis.

[21] Appl. No.: 459,204

[22] Filed: Jun. 2, 1995

[51] Int. Cl.[6] .......... C12M 1/00

[52] U.S. Cl. .......... 435/285.3; 935/85; 89/1.14

[58] Field of Search .......... 435/285.2, 285.3, 435/172.1, 172.3; 935/52, 53, 85; 89/1.14

[56] References Cited

U.S. PATENT DOCUMENTS

| | | | |
|---|---|---|---|
| 4,945,050 | 7/1990 | Sanford et al. | 435/172.1 |
| 5,015,580 | 5/1991 | Christou et al. | 435/172.3 |
| 5,066,587 | 11/1991 | Jones et al. | 435/172.1 |
| 5,120,657 | 6/1992 | McCabe et al. | 435/287 |
| 5,149,655 | 9/1992 | McCabe et al. | 435/287 |
| 5,204,253 | 4/1993 | Sanford et al. | 435/172.3 |
| 5,240,855 | 8/1993 | Tomes | 435/287.1 |
| 5,405,779 | 4/1995 | McCabe et al. | 435/287 |

FOREIGN PATENT DOCUMENTS

0301749A2 5/1988 European Pat. Off. .

OTHER PUBLICATIONS

Klein, T. M., et al., "Particle Gun Technology: A Novel Method for the Introduction of DNA into Living Cells," Abstract for Post 28 in *Biotechnology in Plant Science: Relevance to Agriculture in the Eighties,* International Symposium, Ithaca, NY (1985).

Klein, T. M., et al., "High Velocity Microprojectiles for Delivering Nucleic Acids into Living Cells," *Nature,* 327:70–73 (1987).

Klein, T. M., et al., "Stable Genetic Transformation of Intact *Nicotiana* Cells by the Particle Bombardment Process," *Proc. Natl., Acad. Sci. USA,* 85:8502–8505 (1988).

McCabe, D. E., et al., "Stable Transformation of Soybean (*Glycine max*) by Particle Acceleration," *Bio/Technology,* 6:923–926 (1988).

Sanford, J. C., "The Biolistic Process," *TIBTECH,* 6:299–302 (1988).

Sanford, J. C., et al., "Delivery of Substances into Cells and Tissues Using a Particle Bombardment Process," *Particulate Science and Techn.,* 5:27–38 (1987).

*Primary Examiner*—David A. Redding
*Attorney, Agent, or Firm*—Quarles & Brady

[57] ABSTRACT

An apparatus is disclosed for the genetic transformation of organisms by accelerated particle mediated transformation. Foreign genes are introduced into cells by coating on carrier particles which are physically accelerated into the cells by positioning the carrier particles on the external surface of a carrier ribbon which is wound on a cartridge, the carrier ribbon having an exposed portion. The carrier particles on the exposed portion of the ribbon are displaced and accelerated toward an exit port by a high pressure stream of helium gas. By rotating the ribbon, a continuous supply of carrier particles can be produced and hence large target areas can be transformed without the need to replace the particle carrier. Near the exit port, the gaseous stream is diverted through use of the Coanda effect to divert the gas stream away from a target area. The carrier particles, being much heavier than the gas, continue toward and into the target cells. The treated cells are recovered and a portion of the them contain the foreign gene in their genome.

25 Claims, 5 Drawing Sheets

COANDA EFFECT GENE DELIVERY INSTRUMENT

FIELD OF THE INVENTION

The present invention relates to the general field of genetic engineering of organisms and relates, in particular, to a convenient and easy to use instrument for the insertion of foreign genetic material into the tissue of living organisms.

DESCRIPTION OF THE ART

There is much interest in the general field of the genetic engineering of living organisms. In the genetic engineering of an organism, foreign genetic material, typically a DNA vector constructed so as to express a suitable gene product in the cells of the target organism is transferred into the genetic material cells of the organism, through one of a variety of processes. In the past, the transformation techniques have varied widely. Some of the prior art mechanisms utilized for the insertion of genetic material into living tissues include: direct microinjection; electroporation, a technique in which individual cells are subjected to an electric shock to cause those cells to uptake DNA from a surrounding fluid; liposome-mediated transformation, in which DNA or other genetic material is encapsulated in bilipid vesicles which have an affinity to the cell walls of target organisms; and certain specific types of biological vectors or carriers which have the ability to transfect genetic material carried within them into specific target organisms.

One general technique exists which is applicable to a large range of host organisms. This general technique is referred to as particle mediated genetic transformation. In this technique, the genetic material, be it RNA or DNA, is coated on small carrier particles. The particles are then accelerated toward target cells where the particles impact the cells and penetrate the cell walls, carrying the DNA construct into the cells. Some proportion of the cells into which the genetic material is delivered express the inserted genetic material and another smaller proportion of the cells integrate the delivered DNA into their native genetic material.

One manner of accelerating coated carrier particles utilizes a larger carrier object, sometimes termed macroprojectile. The carrier particles are positioned inside the macroprojectile. The macroprojectile is then accelerated at a high speed toward a stopping plate. Acceleration can be by any suitable means. One means that has proven effective takes advantage of a gunpowder driven device in which the hot gases generated by a gunpowder discharge form a hot gas shock wave which accelerates the macroprojectile. When the macroprojectile strikes the stopping plate having a hole therein, the microprojectiles continue their travel through the hole and eventually strike the target cells. This and other acceleration techniques have been described in U.S. Pat. No. 4,945,050 issued to Sanford et al. and entitled "Method For Transporting Substances Into Living Cells And Tissues And Apparatus Therefore".

A second technique developed for the acceleration of carrier particles was based on a shock wave created by a high voltage electric spark discharge. This technique involves an apparatus having a pair of spaced electrodes placed in a spark discharge chamber. The high voltage discharge is then passed between the electrodes to vaporize a droplet of water placed between the electrodes. The spark discharge vaporizes the water droplet creating a pressure wave, which accelerates a carrier sheet previously placed on the discharge chamber. The carrier sheet carries thereon the carrier particles which are coated with the biological genetic materials. The carrier sheet is accelerated toward a retainer where the carrier sheet is stopped, the particles are separated from it, and only the carrier particles pass on into the biological tissues.

This second technique has been implemented in a hand-held device that can be use for accelerating particles carrying biological materials into large whole organisms which cannot readily be placed on a bench top unit. The hand held device is described in U.S. Pat. No. 5,149,655 issued to McCabe et al. which is entitled "Apparatus For Genetic Transformation".

A variation on that second technique for acceleration of carrier particles was based on an expanding gas shock wave, and a planar surface having carrier particles positioned on the target side of a planar surface. The shock wave that actually impacts the target area is substantially reduced when this technique is utilized. In addition, the apparatus used with this technique does not subject target cells to radiant, heat or appreciable acoustic energy. Hence cell differentiation and successful cell transformation is maximized. This technique is described in U.S. Pat. No. 5,204,253 which issued to Sanford et al. and was entitled "Method and Apparatus For Introducing Biological Substances Into Living Cells."

The apparatus used with this third technique involves a high pressure gas delivery system, a mechanism to generate an instantaneous gas shock out of the high pressure system, an enclosure into which the gas shock is released, contained and vented and a throat region which allows for use of interchangeable planar insertion mechanisms that translate the gas shock into particle acceleration.

When the expanding gas shock is generated it is directed at and impacts a back surface of the planar insertion mechanism (the carrier particles being on the front surface of the insertion mechanism). If the insertion is a fixed membrane and the membrane is allowed to rupture upon application of the shock wave, the particles are disbursed over a wide region of the target cells and much of the shock wave force is absorbed within the ruptured membrane.

All of the techniques discussed above utilized apparatus for the acceleration of carrier particles that can only generate a single potentially traumatic, essentially instantaneous burst of carrier particles (i.e. these are only single shot insertion apparatus). Once the carrier insertion of a single shot apparatus has been utilized it is, for genetic transformation purposes, devoid of carrier particles. In order to utilize any of the single shot apparatus a second time, a new carrier insertion having carrier particles thereon must be installed.

Although single shot apparatus might be ideal for single small area targets, if the cells of a plurality of individual small target areas are to be transformed, unloading and reloading a carrier insertion to prepare for every new transformation is inefficient.

In addition, as transformation technology has evolved past the experimental stage and has become a more commercially useful science, it has become increasingly more important to transform larger target areas. Two limitations inherently exist when a single shot apparatus is used to transform a large surface area target (i.e. a surface larger than the area which subtends a single burst of carrier particles). First, as with a plurality of small target areas, transformation of a large target area may call for a number of reloading steps, each extra step adding to the time necessary to properly transform the target.

Second, uniform transformation across a target area is difficult to accurately achieve with a single shot apparatus. After a first transformation, it is difficult to place a second carrier burst next to the first so as not to leave a gap therebetween or produce a "hot spot" where the two bursts overlap. As more single bursts are employed, proper placement becomes more difficult to achieve. Thirdly, the transformation of a continuous flow of suspended cells would be quite cumbersome, or completely impractical, with a single burst device.

SUMMARY OF THE INVENTION

The present invention is summarized in that an apparatus for injecting a continuous stream of carrier particles carrying DNA into living cells includes a body member having formed therein an acceleration channel along a central axis, the channel having an outlet at an exit end, the body also including formed therein a source chamber adapted to being connected to a source of compressed gas, the source chamber connected to the channel; a particle carrier onto which carrier particles are placed, the particle carrier mounted in the body member in a position exposed to the channel so that a gas stream flowing in the channel can pick up carrier particles off of the particle carrier; and a gas stream diverter placed on the body adjacent the outlet of the channel to divert the gas stream away from the direction of flight of the carrier particles as they exit the body.

It is an object of the present invention to provide a gene delivery instrument based on biologically-coated carrier particles in which the carrier particles are accelerated by a gas stream and in which the gas stream is separated from the carrier particles prior to the carrier particles impacting the target tissues.

It is another object of the present invention to provide a gene gun capable of producing and directing either a continuous flow of DNA coated carrier particles toward relatively large areas of a target organism, or single bursts of carrier particles toward individual target areas with only infrequent reloading.

By providing a carrier receiving ribbon that can be conveyed through the acceleration channel, a continuous supply of carrier particles can be provided to the acceleration channel. As the carrier particles reach the apex of the ribbon guide, the dislodging means frees the particles from the ribbon. The continuous gas stream within the channel moves from the closed end of the channel to the outlet. The freed particles become entrained within the moving gas and are accelerated toward the outlet. A single burst of carrier particles may be produced by conveying the ribbon only a short distance. A continuous flow of particles may be produced by continuously conveying the ribbon.

Also, in the preferred embodiment, the apparatus includes an arcuate surface forming a channel extension on a single peripheral edge of the outlet, the extension being substantially parallel to the channel axis at its proximal end and progressively more perpendicular to the axis at its distal end. As described in more detail below, the channel extension takes advantage of the Coanda effect principal and directs the gas stream emerging from the outlet downward away from the target organism while the heavier DNA coated carrier particles, having gained sufficient momentum, continue along a line parallel to the central axis of the channel (i.e. toward the target area).

Thus, it is another object of the invention to provide an accelerator that may impart high speed velocities to carrier particles directed at a target organism without bombarding the target area with a high velocity gas blast, shock wave, heat, acoustic or radiation energy. The present invention does not utilize accelerating techniques that subject target cells to heat, acoustic or radiation energy and the channel extension operates to direct the high velocity gas stream away from the target area.

Other objects, advantages and features of the present invention will become apparent from the following specification when taken in conjunction with the accompanying drawings.

DETAILED DESCRIPTION OF THE INVENTION

Figure 1:
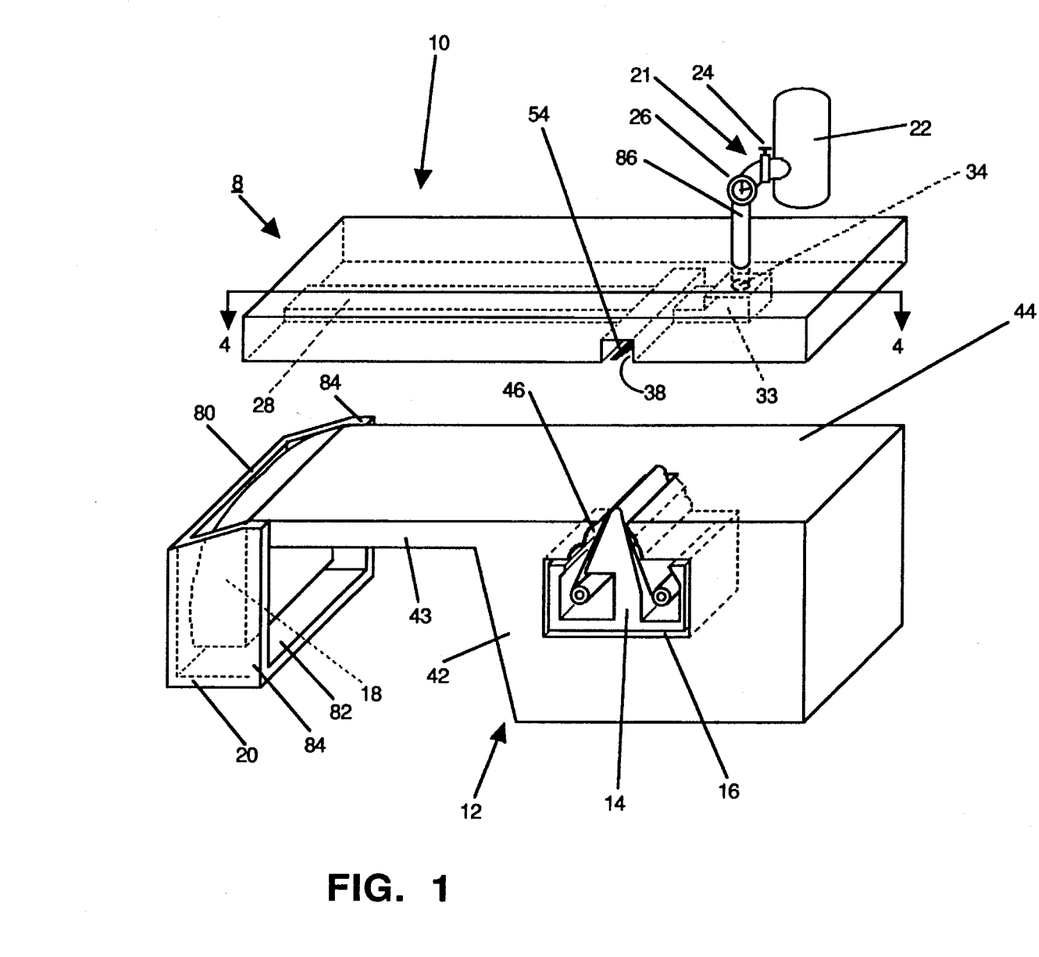
FIG. 1 is an exploded view of the particle acceleration device constructed in accordance with the present invention as utilized to perform continuous cell genetic transformation.

Referring to FIG. 1, the gene delivery instrument 8 of the present invention may be seen to broadly include six main parts: (a) a cover or channel plate 10; (b) a cassette housing 12 having a source chamber 16, the housing 12 serving as the main body of the gene delivery instrument 8; (c) a cassette 14 receivable within the source chamber 16; (d) an arcuate gas stream diverter 18 extending outwardly and downwardly from a distal edge of the cassette housing 12; (e) a dissipator shield 20 attached to a barrel member 43 of the housing 12; and (f) a high pressure gas delivery system 21.

The high pressure gas delivery system 21 includes a source of gas 22 under high pressure. Preferably, the gas is helium, because helium is lightweight and exhibits the characteristic of having a high rate of expansion. Other preferably inert lightweight gasses may also be used, if desired, such as nitrogen. The gas source 22 is provided with a suitable adjustable regulator 24 and pressure indicator 26 providing an adjustable flow of compressed gas to the instrument 8.

Figure 2:
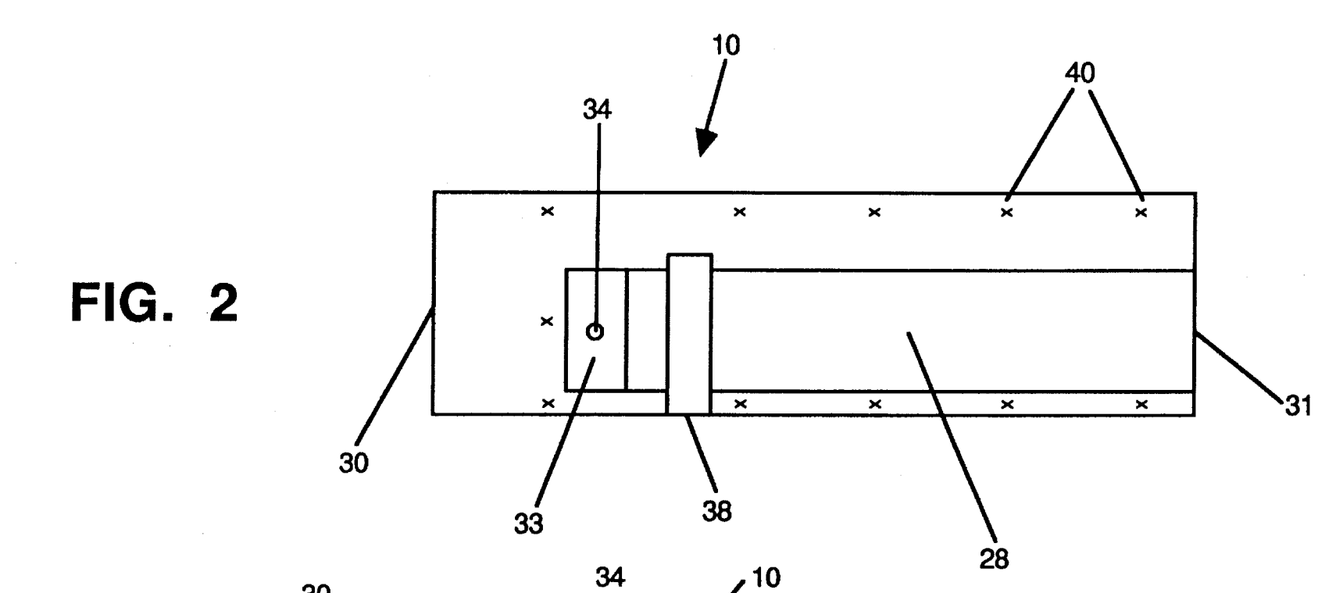
FIG. 2 is a bottom view of the channel plate used in the present invention.
Figure 3:
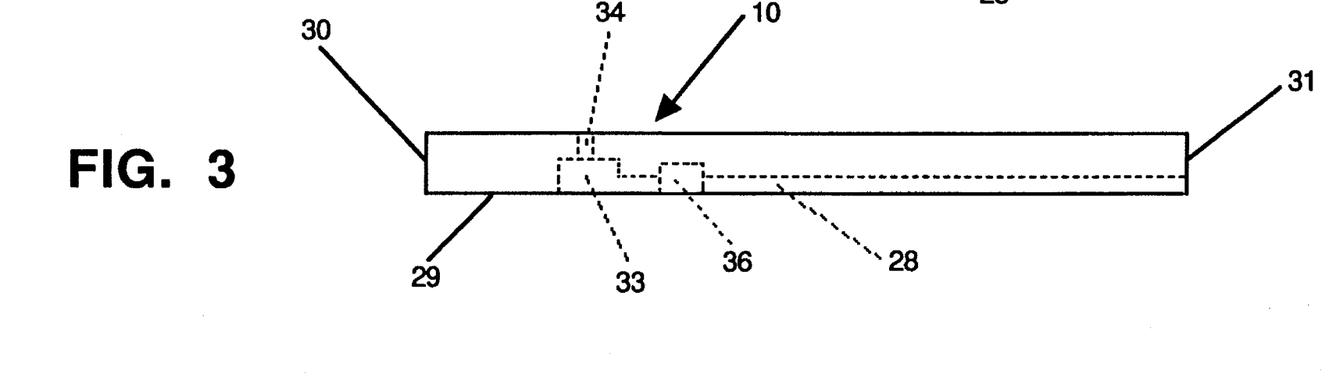
FIG. 3 is a side view of the channel plate shown in FIG. 2.

Referring to FIGS. 2 and 3, the channel plate 10 is largely rectangularly shaped. A rectangular channel groove 28 is formed in the bottom surface 29 of the channel plate 10. The groove 28 extends from an open end 31 opening on the distal end of the channel plate 10 more than one-half the distance to the proximal end of the channel plate 10 and does not extend to either lateral side of the plate 10. A reservoir 33 is provided at the closed end of the groove 28 and a gas port 34, centrally located in the reservoir 33 extends through the thickness of the channel plate 10. A cassette key-way 36 is a channel in the bottom surface 29 of the plate 10 adjacent the sink 33 and extending perpendicular to the length of the groove 28. The keyway 36 extends laterally so as to form an opening 38 in a single lateral side of the channel plate 10. Referring specifically to FIG. 2, the channel plate 10 is provided with a plurality of bolt holes 40 which operate in conjunction with bolts (not shown) to hold the channel plate 10 and the cassette housing 12 together. It should be understood that any suitable means may be employed for attaching the channel plate 10 and cassette housing 12 together.

Referring again to FIG. 1, the high pressure gas system is adapted to be connected to the gas port 34 in the channel plate 10 through suitable tubing 86. In the preferred embodiment, the external shape of the cassette housing 12 is formed so as to be easily gripped and manipulated. Thus, the cassette housing 12, much like a home hair dryer, can have a grip member 42 and a barrel member 43. The top surface 44 of the cassette housing 12 is substantially flat, and thus easily receives the flat bottom surface 29 of the channel plate 10. A source chamber 16 is formed within the grip member 42 and is open to a single lateral side of the grip member 42.

Figure 4:
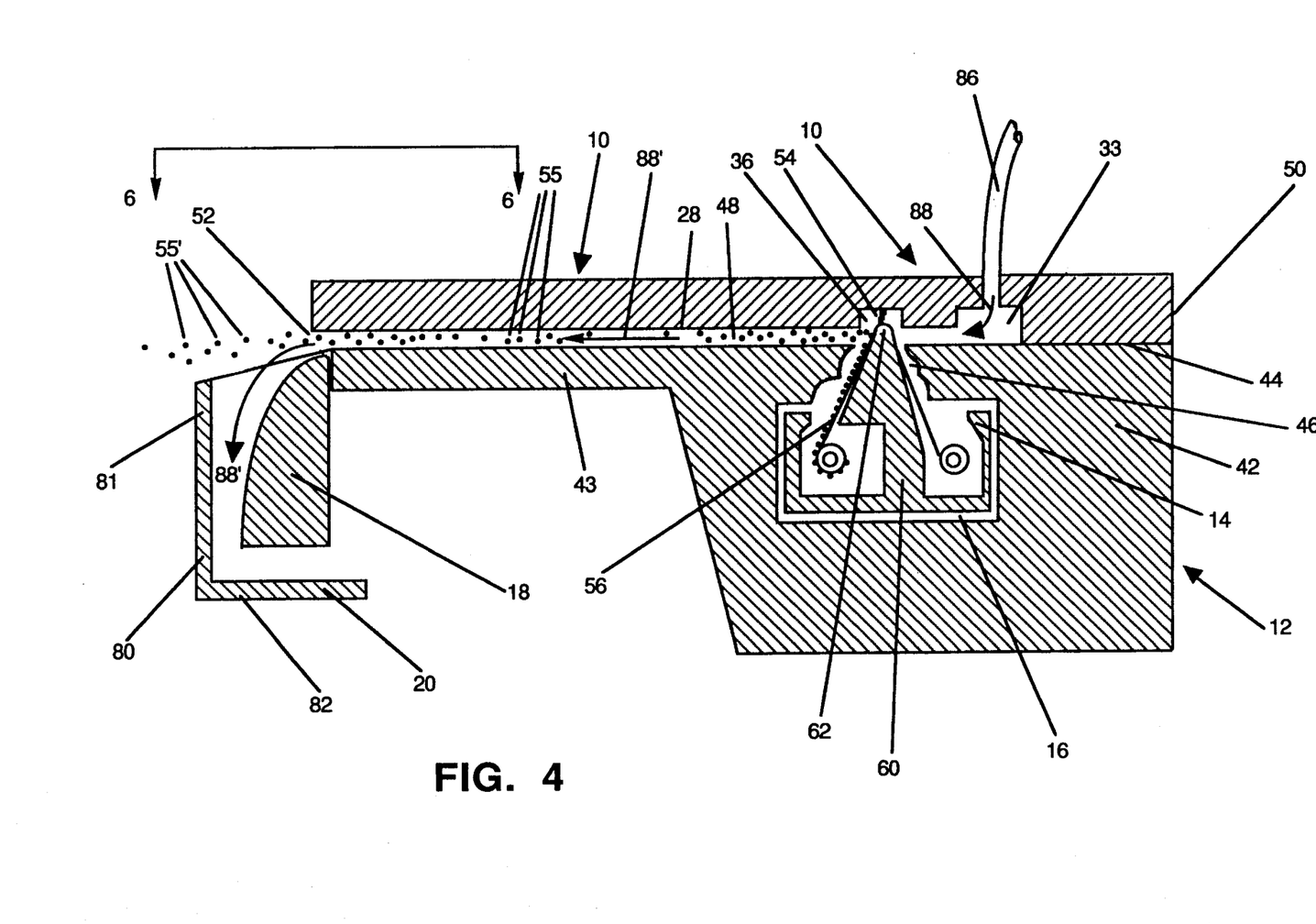
FIG. 4 is a cross-sectional view taken along line 4—4 of FIG. 1 wherein the particle acceleration device is in assembled form.

Referring to FIGS. 1 and 4, a tapered slot 46 extends from the top surface 44 of the grip member 42 downward and into the source chamber 16 below. The slot 46 is of an inverted "v" shape being wide near the source chamber 16 and relatively narrow at the top surface 44.

Referring to FIG. 4, when the channel plate 10 is properly positioned and attached to the cassette housing 12, the top surface 44 of the cassette housing and the channel groove 28 cooperate to from an acceleration channel 48 closed at the proximal end of the instrument 50 and having an outlet 52 at the opposite or distal end of the instrument. In one embodiment, a brush 54 was positioned within the keyway 36 directly above tapered slot 46. The brush 54 was constructed and positioned so as to gently remove carrier particles 55 from a moving ribbon 56 therebelow. It may be appreciated that carrier particles that become lodged within the bristles of the brush 54 are dislodged by the high velocity gas stream 88 moving directly through the bristles toward the outlet 52. Subsequently, it was determined that the brush 54 was not necessary for proper functioning of the instrument, and the brush was removed without adversely affecting performance of the device.

Figure 5:
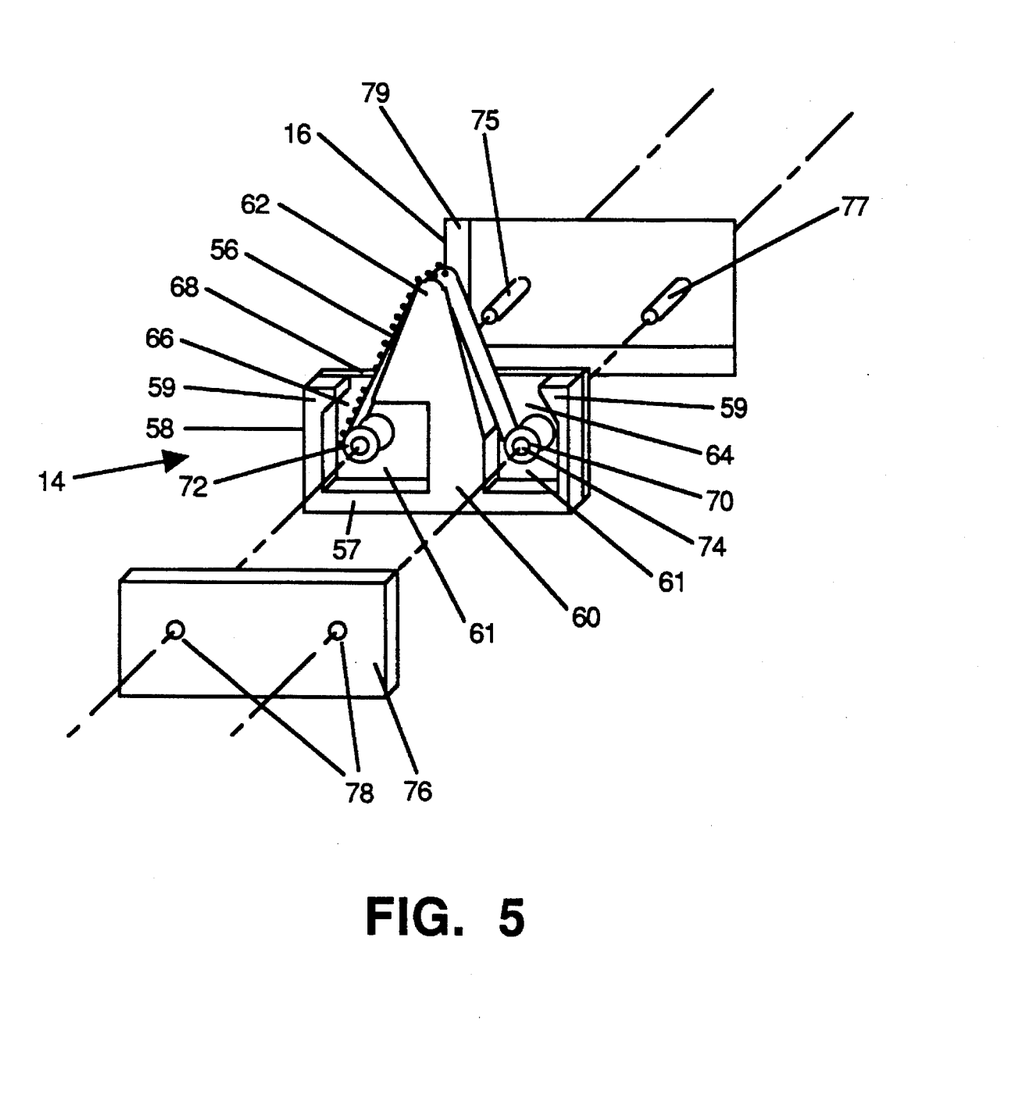
FIG. 5 is an exploded view of a ribbon cassette used in the present invention.
Figure 6A:
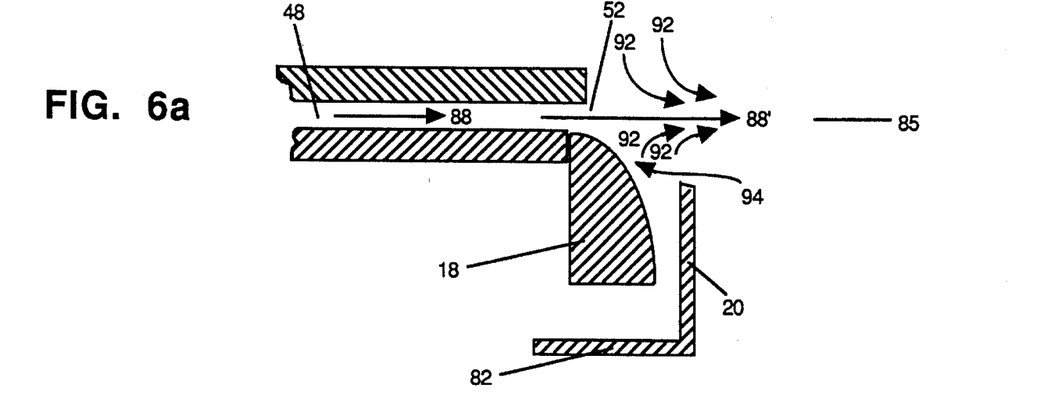
FIGS. 6a–c are cross-sectional views taken along the line 6—6 of FIG. 4 illustrating the Coanda effect principal exploited in the present invention.
Figure 6B:
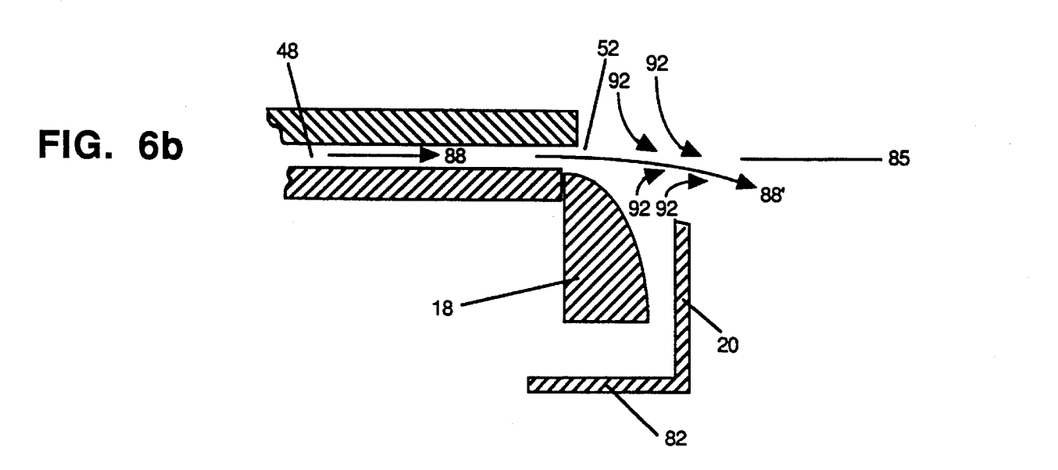
Figure 6C:
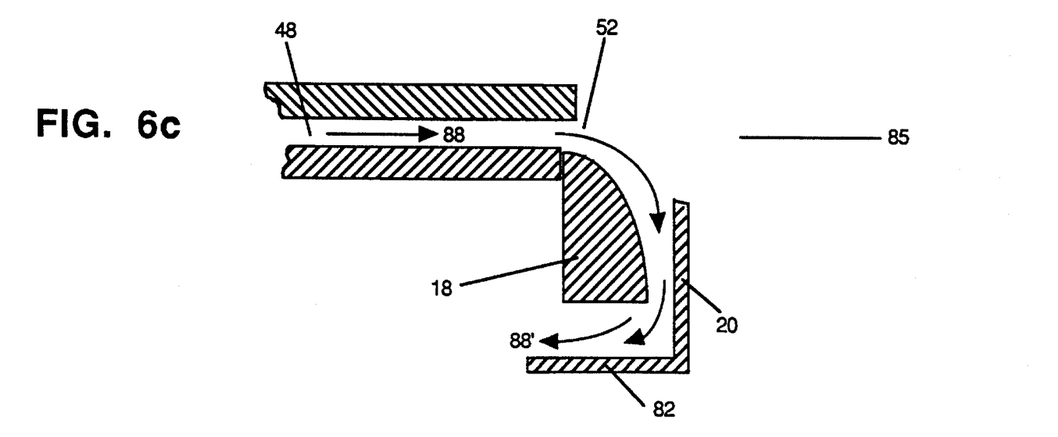

Referring to FIG. 5, the cassette 14 has a ribbon housing 58 which forms a supporting and protecting shell around a ribbon chamber 61 formed therein. The ribbon housing 58 includes a lower wall 57, two opposing upright extensions 59, and a rear wall 68. A guide member 60, centrally located with the ribbon chamber 61, extends upwardly from the lower wall 57 to support an arcuate ribbon guide 62 at its highest point. The guide member 60 divides the ribbon chamber 61 into a reservoir compartment 66 and a take-up compartment 64. A reservoir spool 72 is rotatably attached to the rear wall 68 so as to be centrally located within the reservoir compartment 66. In a like fashion, a take-up spool 70 is centrally positioned within the take-up compartment 64 for rotatable movement. Each spool 70, 72 is a cylindrical shaft with narrowed portions at each end so that it may be secured in place when the instrument is assembled. A cover plate 76, which includes a pair of shallow recesses to receive the narrowed ends of the spools 70 and 72 is provided to cover the lateral side of the instrument over the ribbon chamber 61. A drive shaft 77 extends through the housing of the source chamber 16 to engage the take-up spool 70. A rotary motor such as a small low-speed electric motor or rotary solenoid, is attached to the lateral side of the source chamber and is connected to drive the drive shaft 77. The rotary motor is capable either of stepping the shaft 70 through short rotative movements or of driving the shaft 70 in smooth uniform rotation. Thus, the drive motor can convey the ribbon 56 in a controlled fashion from the reservoir compartment 66 over the ribbon guide 62 and into the take-up compartment 64.

The carrier receiving ribbon 56 used with the invention is a long linear strip of flexible yet strong sheet material. Any number of materials are suitable for use as the ribbon 56. One useful material is a ¾ inch Mylar™ strip (Dupont, Inc. No. 50SMMC2). The length of the strip can be any suitable length, limited only by the distance from the reservoir spool 72 over the guide 62 to the take-up spool 70 and the size of the take-up and reservoir compartments 64, 66. Prior to operation of the gene delivery instrument 8, a previously loaded ribbon 56 is attached by a leading end to the reservoir spool 72 and is wound around the reservoir spool 72 and a portion of the ribbon 56 is extended over the guide 62 and into the take-up compartment 64 where a leading end of the ribbon 56 is attached to the take-up spool 70.

Prior to being wound on the reservoir spool 72, the carrier ribbon 56 must, of course, first be loaded with the biological material to be introduced into the target cells. First the biological material, preferably genetic material such as DNA or RNA, but also possibly proteins, peptides, antigens, hormones, or other biological materials, is coated onto the carrier particles to be used. Prior art techniques used with other accelerated particle instruments can be used to coat the biological material on the carrier particles. The carrier particles themselves must be dense biologically insert particles small in relationship to the size of the target cells. Suitable carrier particles include small gold beads or spheres, 0.1 to 10 microns in size, as well as gold microcrystalline, colloidal, or aggregate materials of irregular shape and size, in which most of the particles in a batch are sized between 0.1 and 10 microns. The particles, once coated with biological material, may be coated onto the carrier ribbon 56 in any manner which is relatively uniform and which does not adhere the particles to the ribbon to fixedly to be removed. It has been found that this can be conveniently done by suspending the DNA coated carrier particles in ethanol, placing the ethanol onto the carrier ribbon 56 which has been extended linearly and placed flat, and then allowing the ethanol to evaporate, thus depositing the carrier particles on the ribbon 56.

The ribbon 56 is then wound onto reservoir spool 72 so that the surface coated with carrier particles 55 forms the outer surface of the winding on the reservoir spool 72. This will ensure that as the ribbon 56 passes over the guide 62, the carrier particle coated surface will be exposed to the gas stream.

After the ribbon 56 has been properly attached wound on the spools 70, 72, the removable cover plate 76 is positioned on the open side of the ribbon housing 58. The cover plate 76 maintains the ribbon 56 within the ribbon housing 58 during operation of the instrument.

Referring again to FIGS. 1 and 4, an arcuate gas stream diverter 18 is provided adjacent to the distal end of the barrel member 43 just below the channel outlet 52. Although the gas stream diverter 18 need not be arcuate, it has been found that the apparatus operates well when an arcuate extension having a 7 mm radius of curvature is employed. The gas stream diverter 18 is particularly helpful to proper operation of the present invention, and its function will be described in more detail below. Note here that the diverter 18 is positioned on the distal end of the housing 12 such that the top edge surface of the diverter 18 is slightly displaced below the lower edge of the channel outlet 52, for reasons that will be discussed below.

A dissipator shield 20 is provided adjacent to and surrounding the gas stream diverter 18. The dissipator shield 20 has a vertically oriented shield member 80 adjacent the housing extension 18 and a horizontal member 82 extending perpendicularly from the vertical member 80 underneath the gas stream diverter 18. The dissipator shield 20 also has two lateral side walls 84 that abut the lateral surfaces of the diverter 18. The side walls 84 are used to attach the shield 20 and the diverter 18 to the barrel member 43 of the housing 12, and also operate in conjunction with the gas stream diverter 18 to use the Coanda effect as described below to divert and dissipate the complex gas stream.

After the apparatus is fully assembled, a cassette 14 with a carrier particle coated ribbon 56 can be positioned inside the source chamber 16. When properly positioned, the ribbon guide 62 will protrude out of the tapered slot 46 and into the cassette keyway 36 above the underside of the channel plate 10. If a brush is used, in this position, the brush 54 should contact the highest portion of the ribbon 56. Preferably, the brush 54 is omitted leaving the peak of the ribbon 56 exposed to any gas stream in the keyway 36.

The portion of the ribbon 56 initially within the keyway 36 may be void of carrier particles 55. Generally, as will be explained below, until a Coanda effect gas flow pattern is established, carrier particles 55 within the acceleration channel 48 are effectively wasted.

Referring to FIG. 4, in operation, after properly preparing a target specimen, tissue, cell, or animal, the pressure regulator 24 may be adjusted so as to generate a steady high velocity gas stream 88 within the acceleration channel 48. Desired carrier velocity dictates necessary gas stream velocity. The velocity to which the carrier particles 55 must be accelerated depends on the size and density of the particles 55 to be accelerated, as well as the nature of the cells to be transformed. Once the type of target cell is known, a properly sized carrier particle 55 may be chosen. Usually, the particles have a diameter between about 100 nanometers and about 10 microns.

Once the properly sized carrier particle 55 is chosen, a corresponding proper velocity may also be chosen. The velocity to which carrier particles 55 are accelerated can be adjusted by adjusting the pressure regulator 24 and can be monitored using the pressure indicator 26. The proper velocity for a given target cell or tissue is adjusted by adjusting the pressure of input gas, and can be empirically determined for any given target tissue.

Referring to FIG. 4, after the desired pressure is adjusted within the acceleration channel 48, and equilibrium is reached within the sink 33, the velocity of the gas stream 88 will be substantially constant. Under these conditions, any particles 55 free within the channel 48 will be accelerated toward the outlet 52.

Referring now to FIGS. 6*a–c*, the present invention takes advantage of the Coanda effect principal, which is sometimes employed in fluidic devices intended for other applications. Under normal conditions, the apparatus of the present invention is operated at an open atmosphere and the helium within the channel 48 is pressurized to about 100 psi. At the moment the pressure regulator 26 is adjusted to allow a gas stream 88 to move down the channel 48, the gas stream 88 exiting the outlet 52 projects in a straight line, substantially coaxially with the channel axis 85. This linear flow is illustrated in FIG. 6a. Referring to FIG. 6*a*, it is important that the arcuate gas stream diverter 18 is provided only on a single side of the outlet 52, in this embodiment the lower side. It is also helpful that the diverter 18 has its top edge displaced very slightly (i.e. approximately 0.1 mm) below the lower edge of the outlet 52. This ensures that the diverter 18 cannot possible divert the gas stream 88 upward and also ensures that a volume of space will be trapped under the gas stream 88 at its point of exit from the outlet 52.

Whenever a stream flows into a body of stagnant air, it entrains some of the surrounding stagnant air and starts it in motion. In the case of the present invention, the ambient air 92 within and above the dissipator shield 20 is entrained and ejected along both sides of the gas stream 88, and replenishing air 94 continuously moves into the regions depleted of air. In other words, areas of low pressure are created above and below the gas stream 88. Above the gas stream 88, the replenishing air moves in unimpeded, and the average pressure along the top surface of the stream 88 remains essentially at ambient atmospheric pressure. However, below the gas stream 88, the flow of replenishing air 94 is restricted by the gas stream diverter 18 and the sides of the dissipator shield 20. Thus, the average pressure below the exiting gas stream 88 will be below atmospheric pressure and a pressure differential will be set up vertically across the gas stream 88.

Referring to FIG. 6b, the resultant differential and pressure across the top and bottom of the existing gas stream 88 causes the gas stream 88 to divert to move closer to the surface of the arcuate gas stream diverter 18. This, in turn, further restricts the area through which the replenishing air can move below the stream 88, making the pressure below the gas stream 88 decrease further, while the differential across the gas stream 88 correspondingly increases.

This action is regenerative, and continues until it terminates with the gas stream 88 essentially following the surface of the arcuate gas stream diverter 18, as best shown in FIG. 6*c*. The gas stream 88 remains close to the arcuate diverter 18 because of the differential pressure impressed upon it.

Once the gas stream diversion is established, the gas stream 88 being directed into the box surrounded by the dissipator shield 20, is further directed away from the target specimen and back toward the grip member 42 of the instrument. In this manner, the target experiences very little gas flow under normal operating conditions and hence undue damage to target cells and surrounding tissue from gas blast is avoided.

Referring to FIG. 4, once the vortex has been established, the pre-prepared target tissue should be properly positioned. Assuming that the target area is large, the outlet 52 of the apparatus should be positioned over one portion of the target. The flow of the gas stream 88 down the channel 28 picks the carrier particles 55 off of the ribbon 56 and carries them out of the outlet 52. The carrier particles 55 exiting the outlet 52 may experience drag in the high density air between the outlet 52 and the target surface. Thus, it may be appropriate to position the instrument close to the target surface, so that the particles experience less drag and are delivered appropriately. A mechanical spacer could be used to provide fixed spacing for that positioning.

After the apparatus is positioned correctly over the target, the driver is energized so that the spools 70, 72 convey the ribbon 56 from the reservoir compartment 66, over the ribbon guide 62 within the acceleration channel 48, and back down into the take-up compartment 64. As the ribbon 56 is conveyed, the portion of the ribbon 56 having carrier particles 55 moves up to the apex of the guide 62 within the keyway 36. The high velocity gas stream 88 picks up the carrier particles off of the ribbon 56 and accelerates the carrier particles 55, now carried in the gas stream 88, toward the channel outlet 52. If the pressure within the acceleration channel 48 was selected properly, the particles 55 should attain the desired velocity by the time they emerge from the outlet 52.

As the gas stream 88, with carrier particles 55, exits the outlet 52, the carrier particles, having a relatively large mass compared to the atoms of the gas stream 88 proceed toward the target under the force of their momentum. The carrier particles 55 are not significantly affected by the Coanda effect operating on the gas stream, due to the higher mass of the carrier particles. Meanwhile, the gas stream 88, under the effects of the Coanda principle described above, is directed downward into the dissipator box 20 and away from the target area. In other words, the gas stream 88 and the carrier particles 55 are separated without significantly diverting the direction of travel of the carrier particles 55. This construction allows the carrier particles 55 to pass to the target, but yet successfully diverts the gas stream flow completely away from the target, thus avoiding any gas impact or trauma to the target tissues.

The device of FIGS. 1–6 above offers two very clear advantages over all known prior art accelerate particle gene delivery instruments. Each of these advantages is appropriate only for certain target tissues or certain applications and each can be implemented in device configurations other than the embodiment of FIGS. 1–6 above. The first advantage is that this device illustrates that, for a device which uses a gas stream to accelerate the carrier particles, the gas stream can be separated from the carrier particles prior to the carrier particles impacting the target tissues. The second advantage is the fact that this device is capable of delivering a large number of carrier particles, either continuously or in multiple independent doses, without the need for reloading the apparatus with an additional particle carrier.

The first advantage, i.e. separation of the particles from the gas stream, is generally useful for gene delivery to animals, but is of particular use in the delivery of biological materials to sensitive tissues or cells which might be injured, moved, or disturbed, by the force of the accelerating gaseous stream. This advantage is enabled by the coanda effect diverter 18 placed adjacent the outlet 52 of the channel 48. This sort of diversion of the exiting gas stream, using the coanda effect, can be used in an instrument that is a "single-shot" device, i.e. that uses a single dose particle carrier rather than a ribbon. It is also envisioned that other geometries for the diverter 18 itself are possible. For example, the diverter 18 could have a series of steps rather than a smooth arcuate surface. The important feature of the diverter 18 is that it influences the gas stream itself to divert, using the coanda effect, while having a minimal effect on the path of travel of the carrier particles themselves.

The second advantageous feature is based on the use of a particle carrier which is elongated and movable so as to be useful either in one very long or several shorter gene delivery applications. By providing a particle carrier which has only a small portion of its extent exposed to the accelerating gas stream at any instant, and by providing a driver to move the particle carrier along to expose a different portion, a much greater amount of particle delivery is enabled without having to disassemble the device to insert a new carrier. This advantageous design is adapted where large amounts of particle delivery are needed, as in the delivery of a large amount of genetic material or of a protein to a patient is desired, and it may also prove advantageous where it is desired to deliver many serial single doses to a series of patients is necessary. Again, this feature is independent of whether or not the coanda effect gas stream diversion is used, since some target tissues, such as intact skin, seem quite capable of withstanding the impact of lower velocity gas streams.

It is to be understood that the present invention is not to be limited to the embodiment shown here, but to encompass all such modified forms thereof as come within the scope of the following claims.

We claim:

1. An apparatus for the delivery of biological material coated onto carrier particles into living cells comprising:

a body member having an elongated acceleration channel formed in it, the channel connecting to an outlet opening from one end of the body member;

a source chamber in the body member adapted to being connected to a source of compressed gas, the source chamber connected to the channel in the body member such that the compressed gas introduced through the source chamber into the channel forms a gas stream flowing in the channel toward the outlet;

a particle carrier onto which the carrier particles are placed, the particle carrier mounted in the source chamber in a position exposed to the channel in the body member so that a gas stream flowing in the channel can pick up carrier particles off of the particle carrier and accelerate the carrier particle toward the outlet; and a gas stream diverter placed on the body member adjacent to the outlet, the diverter shaped and arranged to divert the gas stream from its direction of flow as it exits from the outlet by use of the coanda effect, the diverter not changing substantially the direction of flight of the carrier particles carried in the gas stream, so that the accelerated carrier particles existing from the outlet are substantially separated from the gas stream.

2. An apparatus as claimed in claim 1 wherein the particle carrier is planar.

3. An apparatus as claimed in claim 1 wherein the diverter is arcuate, being curved away from the outlet in the body member.

4. An apparatus as claimed in claim 1 wherein the particle carrier is a ribbon which can be driven so that successive portions of the particle carrier are exposed to the gas stream.

5. An apparatus as claimed in claim 4 further comprising a drive motor in the housing to drive the ribbon.

6. An apparatus as claimed in claim 5 wherein the ribbon is mounted on a cassette for insertion into the housing, the drive motor in connection with the cassette to drive the ribbon.

7. An apparatus as claimed in claim 4 further comprising a ribbon guide to guide the ribbon.

8. An apparatus as claimed in claim 1 further comprising a brush to dislodge the carrier particles from the particle carrier to assist the gas stream in picking up the carrier particles.

9. An apparatus as claimed in claim 1 wherein there is a dissipator shield positioned adjacent to and surrounding the diverter to further channel the gas stream away from the path of travel of the carrier particles.

10. An apparatus for injecting carrier particles carrying DNA into living cells comprising:

a body including formed therein an acceleration channel along a channel axis, the channel having a closed end and an outlet at an exit end, the body also including formed therein a source chamber positioned adjacent the closed end of the channel, the source chamber having an opening into the channel;

a ribbon guide located within the channel above the opening;

a carrier receiving ribbon extending from within the source chamber over the ribbon guide and back into the source chamber, a portion of the ribbon being exposed within the channel;

drive means for moving the ribbon and changing the portion of the ribbon exposed within the channel;

dislodging means for freeing the carrier particles from the portion of the ribbon exposed within the channel;

means for providing a high velocity gas stream within the channel moving from the closed end past the exposed portion of the ribbon and toward the outlet; and whereby, the moving gas stream encounters the carrier particles within the channel and the particles are accelerated toward and eventually emerge from the outlet.

11. The apparatus as recited in claim 10 wherein the source chamber is open to one lateral side of the body and the apparatus further including a cassette positionable within the source chamber, the cassette having a horizontal lower wall, two opposing end walls extending vertically upwardly from the lower wall and a back wall member extending between the two end walls, the ribbon guide including a guide member extending upwardly further than the two end walls from a central portion of the lower wall, the guide member dividing the cassette into a reservoir compartment and a take-up compartment, a reservoir spool centrally positioned within the reservoir compartment and a take-up spool centrally positioned within the take-up compartment, the ribbon connected at a leading end to the reservoir spool and at a trailing end to the take-up spool, a central portion of the ribbon looped over the ribbon guide and exposed above the distal ends of the end walls, the drive means communicating with the take-up spool so as to rotate the spool in a controlled manner.

12. The apparatus as recited in claim 10 further including a channel extension, the extension including an extension surface extending outwardly from a single peripheral edge of the outlet, the extension surface positioned further from the axis than the distance between the axis to the periphery of the outlet, the extension including two vertical side walls, one side wall flush against one lateral edge of the extension surface and the other side wall flush against the other lateral edge of the extension surface.

13. The apparatus as recited in claim 12 wherein the extension surface is an arcuate surface substantially parallel to the axis at its proximal end and progressively more perpendicular to the axis at its distal end.

14. The apparatus as recited in claim 12 further including a dissipator box having a vertical member spaced apart from the channel extension along the channel axis, and a horizontal member extending from a lower end of the vertical member underneath the channel extension.

15. The apparatus as recited in claim 10 wherein the dislodging means is a brush extending from an interior surface of the channel toward the portion of the ribbon inside the acceleration channel, the distal end of the brush making contact with a carrier receiving surface of the ribbon.

16. The apparatus as recited in claim 10 wherein the body includes a gas port through which gas may flow into the interior of the channel and the apparatus further includes a support unit having a source of gas, and an umbilical cord which conducts gas from the source to the gas port.

17. An apparatus for the delivery of biological material coated onto carrier particles into living cells comprising:

a body member having an elongated acceleration channel formed in it, the channel connecting to an outlet opening from one end of the body member, the outlet placed adjacent the target cells;

a source chamber in the body member adapted to being connected to a source of compressed gas, the source chamber connected to the channel in the body member such that the compressed gas introduced through the source chamber into the channel forms a gas stream flowing in the channel toward the outlet;

an elongated particle carrier onto which the carrier particles are placed, the particle carrier mounted in the source chamber in a position so that a portion of the particle carrier is exposed to the channel in the body member so that a gas stream flowing in the channel can pick up carrier particles off of the exposed portion of the particle carrier and accelerate the carrier particles toward the outlet; and a motor connected to the particle carrier to move the particle carrier to change the portion of the particle carrier exposed to the channel so that additional carrier particles can be delivered without removing the particle carrier from the apparatus.

18. An apparatus as claimed in claim 17 wherein the particle carrier is a planar ribbon and the motor moves the particle carrier by winding the ribbon to expose differing portions of the ribbon to the channel.

19. An apparatus as claimed in claim 18 wherein the ribbon is wound on a pair of spools an the motor moves the ribbon by winding the ribbon onto a one of the spools.

20. An apparatus as claimed in claim 18 wherein the motor is an electric motor.

21. A method for the acceleration of carrier particles carrying biological material thereon comprising the steps of:

(a) placing the carrier particles on an elongated particle carrier;

(b) placing the particle carrier in a gene delivery instrument having a body member with an elongated acceleration channel formed in it ending in an outlet opening from one end of the body member, the particle carrier placed in the body member in such a fashion that a portion of the particle carrier is exposed to a gas stream passing through the channel so that the carrier particles on that portion of the particle carrier will be picked off the particle carrier by the gas stream in the channel and carried toward the outlet;

(c) introducing a stream of compressed gas into the channel in the body of the instrument so that the compressed gas causes a gas stream to flow through the channel toward and through the outlet, the gas stream picking up and accelerating the carrier particles off of the portion of the particle carrier as the gas stream travels toward the outlet; and (d) moving the particle carrier to expose a different portion of the particle carrier to the gas stream without removing the particle carrier from the apparatus.

22. A method as claimed in claim 21 wherein the motor moves the particle carrier while the gas stream is passing through the channel.

23. A method as claimed in claim 21 wherein the particle carrier is a ribbon wound on a pair of spools and the step of moving the particle carrier is performed by winding the particle carrier onto a one of the spools.

24. A method for the acceleration of carrier particles carrying biological material thereon comprising the steps of:

(a) placing the carrier particles on a particle carrier;

(b) placing the particle carrier in a gene delivery instrument having a body member with an elongated acceleration channel formed in it ending in an outlet opening from one end of the body member, the particle carrier placed in the body member in such a fashion that the carrier particles on the particle carrier are exposed to a gas stream passing through the channel;

(c) introducing a stream of compressed gas into the channel in the body of the instrument so that the compressed gas causes a gas stream to flow through the channel toward and through the outlet, the gas stream picking up and accelerating the carrier particles as it travels; and (d) separating the accelerated carrier particles from the gas stream as it exits the outlet by diverting the gas stream using the coanda effect to divert the gas stream without substantially diverting the travel of the carrier particles.

25. A method as claimed in claim 24 wherein the particle carrier is a ribbon and the method further includes the step of moving successive portions of the ribbon into exposure to the gas stream in the channel.

* * * * *